United States Patent [19]

Matsumura et al.

[11] 4,435,594

[45] Mar. 6, 1984

[54] PROCESS FOR THE PREPARATION OF METHACRYLIC ACID ESTERS

[75] Inventors: Hiroshi Matsumura; Fumiki Murakami; Hiroshi Sonobe, all of Otake, Japan

[73] Assignee: Minemet Recherche, Trappes, France

[21] Appl. No.: 89,497

[22] Filed: Oct. 30, 1979

[30] Foreign Application Priority Data

Oct. 31, 1978 [JP] Japan ................................ 53-133858

[51] Int. Cl.$^3$ ............................................. C07C 67/48
[52] U.S. Cl. ..................................... 560/205; 560/218
[58] Field of Search ................... 560/205, 218; 203/43

[56] References Cited

U.S. PATENT DOCUMENTS

| | | | |
|---|---|---|---|
| 3,157,693 | 11/1964 | Wheeler et al. | 560/218 |
| 3,261,767 | 7/1966 | Knorr et al. | 560/218 |
| 3,776,947 | 12/1973 | Shimizu et al. | 560/205 |
| 4,142,058 | 2/1979 | Matsumura et al. | 203/43 |

*Primary Examiner*—Natalie Trousof
*Assistant Examiner*—L. Hendriksen
*Attorney, Agent, or Firm*—Fleit, Jacobson, Cohn & Price

[57] ABSTRACT

A process for preparing a methacrylic acid ester by reacting methacrylic acid with a lower aliphatic alcohol in the liquid phase using a solid acid catalyst at a molar ratio of alcohol to methacrylic acid of 1.2–3.0 and a reaction temperature of 70°–100° C. is improved by (1) extracting the unreacted alcohol from the reaction mixture with an aqueous solvent at a temperature of 25° to 70° C.,
(2) removing the low boiling substances from the extraction residual mixture by distillation, whereby an organic residue is generated containing methacrylic acid ester and unreacted methacrylic acid, and
(3) separating the unreacted methacrylic acid and the methacrylic acid ester by distillation.

6 Claims, 1 Drawing Figure

PROCESS FOR THE PREPARATION OF METHACRYLIC ACID ESTERS

BACKGROUND OF THE INVENTION

1. Field of the Invention

The present invention relates to a process for the preparation of methacrylic acid esters by esterification of methacrylic acid with a lower aliphatic alcohol.

2. Description of the Prior Art

In preparing methacrylic acid esters in the liquid phase, using an acidic solid catalyst, the reaction product contains large amounts of unreacted methacrylic acid because the esterification reaction is an equilibrium reaction. Therefore it is necessary to separate unreacted methacrylic acid from the esterification product in order to reuse it as the raw material of the esterfication reaction.

According to the prior art, after separating unreacted methacrylic acid from the esterification product by distillation or flash vaporization (methacrylic acid separation step), unreacted alcohol is separated, and then the methacrylic acid ester is rectified. (Japanese Patent Publication No. 1369/73). The above method, however, has certain disadvantages because the formed ester, water and unreacted alcohol must be all vaporized in the methacrylic acid separation step in order to separate unreacted methacrylic acid.

Hence a need has continued to exist for an improved process for separating methacrylic acid from the esterfication reaction mixture.

SUMMARY OF THE INVENTION

Accordingly, it is an object of the invention to provide an improved process for preparing methacrylic acid esters by esterification of methacrylic acid with lower aliphatic alcohols.

A further object of the invention is to provide a process for separating methacrylic acid from the reaction mixture resulting from the esterification of the acid with a lower aliphatic alcohol, which does not require the vaporization of all the ester, water, and unreacted alcohol.

The inventors of the present invention have conducted various studies in an effort to economically and advantageously carry out esterification of the methacrylic acid with a lower aliphatic alcohol and produce purified methacrylic acid esters, and have found the fact that the aforementioned methacrylic acid separation step can be eliminated if the esterification is carried out under limited conditions and the alcohol extracting column is operated under particular conditions and have thus accomplished the present invention.

That is, the gist of the present invention resides in an improved process for the preparation of methacrylic acid ester comprising reacting methacrylic acid with a lower aliphatic alcohol in the liquid phase, using an acidic solid catalyst at a molar ratio of alcohol to methacrylic acid of 1.2 to 3.0 and at a reaction temperature of 70° to 100° C., the improvement characterized by directly feeding the esterification product into an alcohol extracting column maintained at 25° to 70° C. to separate unreacted alcohol, removing low boiling substances, separating unreacted methacrylic acid as bottoms of the refining column for methacrylic acid esters, and recycling methacrylic acid to the esterification step.

In removing the low boiling substances in a distilling column, it is desirable to take out the water phase from the distillate of the column, while permitting the organic phase to reflux.

BRIEF DESCRIPTION OF THE DRAWING

A more complete appreciation of the invention and many of the attendant advantages thereof will be readily attained as the same becomes better understood by reference to the following detailed description when considered in connection with the accompanying drawings, wherein.

DETAILED DESCRIPTION OF THE PREFERRED EMBODIMENTS

Figure 1:
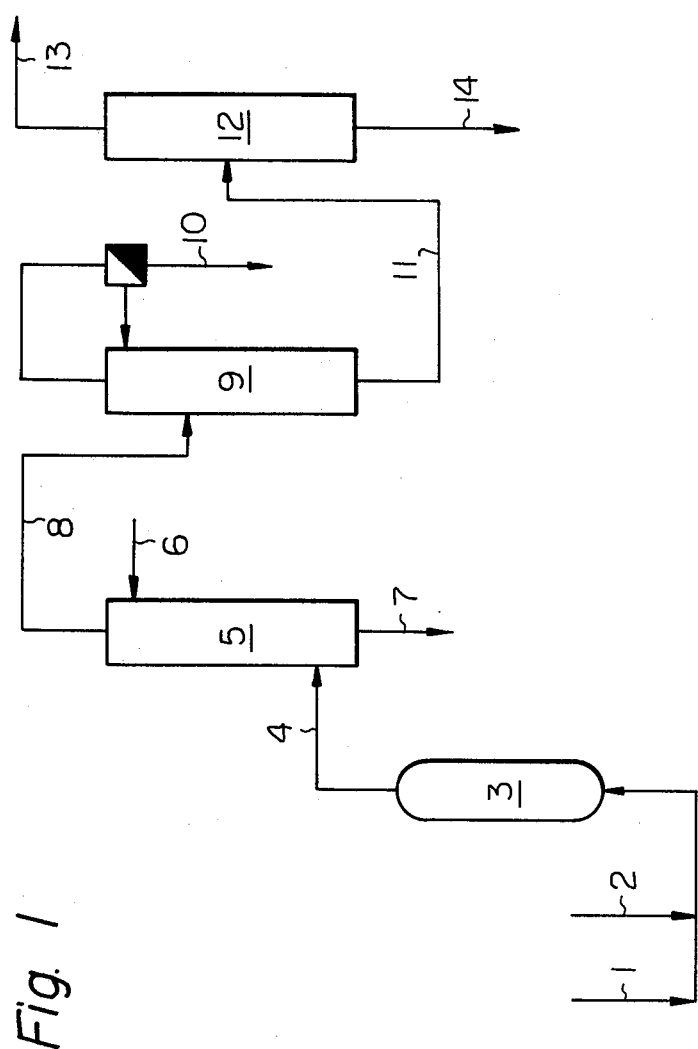
FIG. 1 shos a flow chart of a process employing the method of the present invention.

One embodiment of the present invention is concretely illustrated below for each of the steps.

Preferred examples of the acidic solid catalyst are sulfonic acid type cation-exchange resins of the polystyrene type. More concretely speaking, they may be Amberlites IR-118, IR-120, IR-200 (Products of Rhom & Haas Co.) Diaions PK-208, PK-228, SK-102 (Products of Mitsubishi Kasei Co.), DOW-50 (Product of Dow Co.), and the like.

The lower aliphatic alcohols to be esterified with methacrylic acid are those having not more than three carbon atoms such as methyl alcohol, ethyl alcohol, or isopropyl alcohol.

The lower aliphatic alcohol is used at a molar ratio with respect to the methacrylic acid (alcohol/acid) of 1.2–3.0 and the reaction temperature is from 70° to 100° C. Further, it is desirable that the conversion of methacrylic acid into ester thereof should be greater than 60%.

The thus obtained esterification product is directly supplied to an alcohol extracting column where it is brought into contact in a counter current flow with a solvent consisting mainly of water, such that the unreacted alcohol and formed water are separated. Pure water may be used or water containing small amounts of impurities such as the alcohols or acids used as reagents, or the esterification product is also used. Pure water is preferred, but small amounts of the impurities can be tolerated so long as the density of the aqueous extractant remains sufficiently different from that of the reaction mixture so that proper separation of phases occurs in the extraction column. What is important in this process is the operation of the alcohol extracting column which can be operated only when the temperature of the column is 25° C. or higher. It is difficult to define all of the factors which determine whether the operation of the extracting column is possible or not.

Table 1 shows the relation of the temperatures and the specific gravity differences between organic phase and water phase at the top or bottom of the alcohol extracting column.

TABLE 1

| Temperature (°C.) | Difference in specific gravities at the top of alcohol extracting column | Difference in specific gravities at the bottom of alcohol extracting column |
|---|---|---|
| 20 | 0.0324 | 0.0299 |
| 30 | 0.0403 | 0.0343 |
| 40 | 0.0484 | 0.0385 |
| 50 | 0.0564 | 0.0439 |

As will be obvious from Table 1, the higher the extracting temperature, the greater the specific gravity difference. In other words, the operation becomes easier at higher temperatures.

If the temperature is lower than 25° C., the specific gravity difference (the difference in specific gravities of two phases) becomes very small, whereby the liquid is emulsified making it impossible to separate the two phases by extraction.

This emulsification seems to be caused not only by the reduced difference in specific gravities but also by the presence of the unreacted methacrylic acid which completely dissolves in both phases, and the increased viscosity at lower temperatures. On the other hand, too high a temperature may cause polymerization.

From an industrial point of view therefore, it is necessary to employ an extracting temperature of 25° C. to 70° C. The temperature is, preferably, between about 30° and 70° C., most preferably, the temperature is between 40° and 60° C.

Moreover, since the presence of the unreacted methacrylic acid adversely affects the separation of two phases as mentioned above, it is desired that the conversion of methacrylic acid in the esterification step be greater than 60%.

In the second step, the water and low boiling substances are removed from the ester phase, now devoid of alcohol, in a distilling column for removing low boiling substances. The distillate from the column separates into an organic phase and a water phase. The organic phase is permitted to reflux, and only the water phase is taken out to remove the low boiling substances to a sufficient degree.

As a result, only the methacrylic acid ester dissolved in the water phase is lost in the low boiling substance removing column. This contributes to the increase in the yield of the purified methacrylic acid ester.

In the third step, the ester and methacrylic acid are separated in the distilling column for refining the ester. Here, due to a great difference in boiling point, the ester and methacrylic acid are easily separated by a conventional distilling operation.

The separated methacrylic acid is obtained as the bottoms of the ester refining column and is reused as a raw material for the esterification reaction.

FIG. 1 shows one embodiment of a process for preparing methacrylic acid ester employing the method of the present invention.

The process will be explained below with reference to the drawing.

Methacrylic acid and an alcohol are fed via (1) and (2) into an esterification reactor (3).

The esterification products are taken out via (4) and fed to an alcohol extracting column (5), while a solvent which is an alcohol-extracting agent is fed to the column via (6).

Counter-current extraction is carried out in the column (5), from which an ester phase is taken out via (8) and an extraction phase is take out via (7).

The ester phase is sent via (8) to the distilling column (9) for removing low-boiling substances. The distillate is separated into an organic phase and a water phase, the former being permitted to reflux and the latter being taken out via (10). Bottoms from the distilling column (9) are sent via (11) to the distilling column (12) for purifing methacrylic acid ester. From (13), the distillate of purified ester is obtained and from (14), the bottoms fraction of recovered methacrylic acid is obtained. In the above process, the recovered methacrylic acid can be recycled to the esterification reactor.

In the present invention, various types of extracting column can be used for the counter-current extraction.

It is especially preferable to use extracting columns having a plurality of discs, propellers or other shaped rotors.

Thus, the process of the present invention is simple and rational as compared with the hitherto conventional processes, and makes it possible to prepare pure methacrylic acid esters in high yield and at a reduced cost.

Having generally described the invention, a more complete understanding can be obtained by reference to certain specific examples, which are provided herein for purposes of illustration only and are not intended to be limiting unless otherwise specified.

The percentages in the example are all by weight.

EXAMPLE 1

Raw materials shown in Table 2 were supplied at a rate of 2.0 kg/hr into an esterification reactor charged with 2.4 l of sulfonic acid-type cation exchange resin, and the esterification reaction was carried out at 85° C. to obtain an esterification product having the composition as shown in Table 2.

TABLE 2

| Component | Raw material for esterification | Esterification product |
|---|---|---|
| Methanol | 31.5% | 16.1% |
| Methyl methacrylate | 6.2 | 55.0 |
| Water | 0.5 | 9.0 |
| Methacrylic acid | 58.3 | 16.4 |
| Others | 3.5 | 3.5 |

The reaction product which was taken out from the reactor was cooled to 45° C., and was introduced near the bottom of a 40-stage rotary disc extracting column of 4.6 cm diameter and 76 cm height, at a rate of 2.0 kg/hr.

A solvent having the composition shown in Table 3 was introduced near the top of the column at a rate of 1.24 kg/hr, and an ester phase having the composition shown in Table 3 was obtained from the top of the column at a rate of 1.46 kg/hr.

TABLE 3

| Component | Solvent (extracting agent) | Ester phase |
|---|---|---|
| Methanol | — | 0.05% |
| Methyl methacrylate | — | 72.4 |
| Water | 95.3% | 5.5 |
| Methacrylic acid | 4.5 | 22.0 |
| Others | 0.2 | 0.05 |

Then, the ester phase was distilled in a 30 stage glass Oldershaw type distilling column of 4.1 cm in diameter at a pressure of 350 mmHg, at a head temperature of 60° C., and a pot temperature of 87° C., to give a distillate at a rate of 81.7 gr/hr and bottoms at a rate of 1.38 kg/hr, having the composition shown in Table 4.

Low boiling substances such as methanol, methyl acrylate, methyl acetate or the like were not detected in the bottoms fraction.

TABLE 4

| Component | Distillate | Bottoms fraction |
|---|---|---|
| Methanol | 0.89% | — |
| Methyl | 0.76 | 76.65% |

TABLE 4-continued

| Component | Distillate | Bottoms fraction |
| --- | --- | --- |
| methacrylate | | |
| Water | 98.25 | — |
| Methacrylic acid | — | 23.3 |
| Others | 0.1 | 0.05 |

The bottoms were distilled in a 30 stage glass Oldershaw type distilling column of 4.6 cm in diameter at a pressure of 100 mmHg, at a head temperature of 45.5° C., a pot temperature of 88° C. and reflux ratio of 0.5, to give a distillate of pure methyl methacrylate at a rate of 0.975 kg/hr and bottoms at a rate of 0.405 kg/hr, having the composition as shown in Table 5.

TABLE 5

| Component | Distillate | Bottoms |
| --- | --- | --- |
| Methyl methacrylate | 99.97% | 20.51% |
| Methacrylic acid | — | 79.39 |
| Others | 0.03 | 0.1 |

Having now full described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing a methacrylic acid ester by reacting methacrylic acid with a lower aliphatic alcohol in the liquid phase using a solid acidic catalyst at a molar ratio of alcohol to methacrylic acid of 1.2–3.0:1 and a reaction temperature of 70°–100° C., the improvement comprising: (1) extracting substantially only the unreacted alcohol from the reaction mixture containing unreacted alcohol, unreacted methacrylic acid, ester product and impurities with an aqueous solvent at a temperature of 40° to 60° C.; (2) removing the low boiling substances and water from the extraction-residual mixture by distillation whereby an organic residue is generated containing methacrylic acid ester and unreacted methacrylic acid; and (3) separating said unreacted methacrylic acid and said methacrylic acid ester by distillation.

2. The process of claim 1 further comprising recycling the unreacted methacrylic acid to the esterification reaction.

3. The process of claim 1 wherein said low boiling substances are removed by distillation wherein a distillate is produced having an organic phase and an aqueous phase and said organic phase is totally refluxed while said aqueous phase is separated.

4. The process is claim 1 wherein the conversion of methacrylic acid into methacrylic ester is greater than 60%.

5. The process of claim 1 wherein said aqueous solvent is pure water.

6. The process of claim 1 wherein said lower aliphatic alcohol is selected from the group consisting of methyl alcohol, ethyl alcohol and isopropyl alcohol.

* * * * *

UNITED STATES PATENT AND TRADEMARK OFFICE
CERTIFICATE OF CORRECTION

PATENT NO. : 4,435,594

DATED : March 6, 1984

INVENTOR(S) : Matsumura et al.

It is certified that error appears in the above-identified patent and that said Letters Patent is hereby corrected as shown below:

On the title page Item /73/ should be deleted to read as follows:
-- [73] MITSUBISHI RAYON CO., LTD., Tokyo, JAPAN --

On the title page Attorney, Agent or Firm should be deleted to read as follows:
-- Attorney, Agent, or Firm -- OBLON, FISHER, SPIVAK, McCLELLAND & MAIER, P.C. --

Signed and Sealed this

Eleventh Day of December 1984

[SEAL]

Attest:

GERALD J. MOSSINGHOFF

Attesting Officer

Commissioner of Patents and Trademarks